(12) United States Patent
Heneghan et al.

(10) Patent No.: US 10,885,152 B2
(45) Date of Patent: Jan. 5, 2021

(54) SYSTEMS AND METHODS FOR MONITORING QUALITY OF LIFE PARAMETERS USING NON-CONTACT SENSORS

(71) Applicant: ResMed Sensor Technologies Limited, Dublin (IE)

(72) Inventors: Conor Heneghan, San Diego, CA (US); Conor Hanley, Dun Laoghaire (IE); Niall Fox, Tullamore (IE); Alberto Zaffaroni, Dublin (IE); Philip De Chazal, Dublin (IE)

(73) Assignee: RESMED SENSOR TECHNOLOGIES LIMITED, Dublin (IE)

(*) Notice: Subject to any disclaimer, the term of this patent is extended or adjusted under 35 U.S.C. 154(b) by 481 days.

(21) Appl. No.: 14/947,777

(22) Filed: Nov. 20, 2015

(65) Prior Publication Data

US 2016/0125160 A1 May 5, 2016

Related U.S. Application Data

(63) Continuation of application No. 13/120,640, filed as application No. PCT/US2009/058020 on Sep. 23, 2009, now Pat. No. 9,223,935.

(60) Provisional application No. 61/099,792, filed on Sep. 24, 2008.

(51) Int. Cl.
| G06F 19/00 | (2018.01) |
| A61B 5/00 | (2006.01) |
| G16H 50/30 | (2018.01) |
| G16H 50/20 | (2018.01) |
| G16H 10/20 | (2018.01) |

(52) U.S. Cl.
CPC ............ *G06F 19/36* (2013.01); *A61B 5/0002* (2013.01); *A61B 5/4806* (2013.01); *A61B 5/4815* (2013.01); *A61B 5/72* (2013.01); *A61B 5/7271* (2013.01); *A61B 5/74* (2013.01); *G06F 19/3418* (2013.01); *G16H 10/20* (2018.01); *G16H 50/20* (2018.01); *G16H 50/30* (2018.01)

(58) Field of Classification Search
None
See application file for complete search history.

(56) References Cited

U.S. PATENT DOCUMENTS

| 2,634,413 A | 4/1953 | Potter |
| 3,796,208 A | 3/1974 | Bloice |
| 3,911,899 A | 10/1975 | Hattes |
| 3,993,995 A | 11/1976 | Kaplan et al. |
| 4,085,740 A | 4/1978 | Allen, Jr. |
| 4,513,748 A | 4/1985 | Nowogrodzki et al. |
| 4,958,638 A | 9/1990 | Sharpe et al. |
| 5,314,037 A | 5/1994 | Shaw et al. |
| 5,361,070 A | 11/1994 | McEwan |
| 5,549,113 A | 8/1996 | Halleck et al. |
| 5,573,012 A | 11/1996 | McEwan |
| 5,590,650 A | 1/1997 | Genova |
| 5,671,733 A | 9/1997 | Raviv et al. |
| 5,766,208 A | 6/1998 | McEwan |
| 5,902,250 A | 5/1999 | Verrier et al. |
| 5,966,090 A | 10/1999 | McEwan |
| 5,995,856 A | 11/1999 | Nellcor |
| 6,011,477 A | 1/2000 | Teodorescu et al. |
| 6,062,216 A | 5/2000 | Corn |
| 6,132,371 A | 10/2000 | Dempsey et al. |
| 6,146,332 A | 11/2000 | Pinsonneault et al. |
| 6,359,597 B2 | 3/2002 | Haj-Yousef |
| 6,492,933 B1 | 12/2002 | McEwan |
| 6,834,251 B1 | 12/2004 | Fletcher |
| 6,839,581 B1 | 1/2005 | El-Solh et al. |

(Continued)

FOREIGN PATENT DOCUMENTS

| CN | 1737857 A | 2/2006 |
| CN | 1739451 A | 3/2006 |

(Continued)

OTHER PUBLICATIONS

Morin, C. M., et al; "Psychological and Behavioral Treatment of Insomnia: Update of the Recent Evidence (1998-2004)"; Sleep, vol. 29, No. 11, 2006; p. 1398-1414.*

Tang, P. C. et al; "Personal Health Records: Definitions, Benefits and Strategies for Overcoming Barriers to Adoption"; Journal of the American Medical Informatics Association vol. 13 No. 2 Mar. / Apr. 2006 (Year: 2006).*

Lane, S. J. et al; "A review of randomized controlled trials comparing the effectiveness of hand held computers with paper methods for data collection"; BMC Medical Informatics and Decision Making 2006, 6:23; p. 1-10 (Year: 2006).*

(Continued)

*Primary Examiner* — G Steven Vanni
(74) *Attorney, Agent, or Firm* — Botos Churchill IP Law LLP

(57) ABSTRACT

An apparatus, system, and method for the measurement, aggregation and analysis of data collected using non-contact or minimally-contacting sensors provides quality of life parameters for individual subjects, particularly in the context of a controlled trial of interventions on human subjects (e.g., a clinical trial of a drug, or an evaluation of a consumer item such as a fragrance). In particular, non-contact or minimal-contact measurement of quality-of-life parameters such as sleep, stress, relaxation, drowsiness, temperature and emotional state of humans may be evaluated, together with automated sampling, storage, and transmission to a remote data analysis center. One component of the system is that the objective data is measured with as little disruption as possible to the normal behavior of the subject. The system can also support behavioral and pharmaceutical interventions aimed at improving quality of life.

31 Claims, 8 Drawing Sheets

(56) References Cited

U.S. PATENT DOCUMENTS

| | | |
|---|---|---|
| 6,932,769 B2 | 8/2005 | Griffin et al. |
| 7,009,561 B2 | 3/2006 | Menache |
| 7,196,629 B2 | 3/2007 | Ruoss et al. |
| 7,199,749 B2 | 4/2007 | Greneker, III et al. |
| 7,272,431 B2 | 9/2007 | McGrath |
| 7,387,607 B2 | 6/2008 | Holt et al. |
| 7,428,468 B2 | 9/2008 | Takemura et al. |
| 7,468,034 B2 | 12/2008 | Ouchi |
| 7,473,228 B2 | 1/2009 | Griffin et al. |
| 7,524,279 B2 | 4/2009 | Auphan |
| 7,542,878 B2 | 6/2009 | Nanikashvili |
| 7,679,545 B2 | 3/2010 | Rausch et al. |
| 7,898,455 B2 | 3/2011 | Rosenbury |
| 7,956,755 B2 | 6/2011 | Lee et al. |
| 8,026,840 B2 | 9/2011 | Dwelly et al. |
| 8,120,462 B2 | 2/2012 | Shafer |
| 8,398,538 B2 | 3/2013 | Dothie et al. |
| 8,428,696 B2 | 4/2013 | Foo |
| 8,454,528 B2 | 6/2013 | Yuen et al. |
| 2003/0092975 A1 | 5/2003 | Casscells et al. |
| 2003/0201894 A1 | 10/2003 | Li |
| 2004/0034289 A1 | 2/2004 | Teller et al. |
| 2004/0073098 A1 | 4/2004 | Geva et al. |
| 2004/0122489 A1 | 6/2004 | Mazar et al. |
| 2004/0210155 A1 | 10/2004 | Takemura |
| 2004/0225179 A1* | 11/2004 | Kaplan ............... A61B 5/4809 600/26 |
| 2004/0249258 A1 | 12/2004 | Tupin et al. |
| 2004/0249296 A1 | 12/2004 | Ellscheid et al. |
| 2005/0042589 A1 | 2/2005 | Hatlestad et al. |
| 2005/0043645 A1 | 2/2005 | Ono et al. |
| 2005/0073424 A1 | 4/2005 | Ruoss et al. |
| 2005/0076908 A1 | 4/2005 | Lee et al. |
| 2005/0113650 A1 | 5/2005 | Pacione et al. |
| 2005/0119532 A1 | 6/2005 | Cloutier |
| 2005/0119711 A1 | 6/2005 | Cho et al. |
| 2005/0128124 A1 | 6/2005 | Greneker et al. |
| 2005/0143617 A1 | 6/2005 | Auphan |
| 2005/0240087 A1 | 10/2005 | Keenan et al. |
| 2006/0074334 A1* | 4/2006 | Coyle ............... A61B 5/0476 600/529 |
| 2006/0079164 A1 | 4/2006 | DeCastro et al. |
| 2006/0111635 A1 | 5/2006 | Todros et al. |
| 2006/0183980 A1* | 8/2006 | Yang ............... A61B 5/6804 600/301 |
| 2006/0189924 A1 | 8/2006 | Blakley et al. |
| 2006/0241510 A1 | 10/2006 | Halperin et al. |
| 2006/0247505 A1 | 11/2006 | Siddiqui |
| 2006/0270941 A1 | 11/2006 | Xie et al. |
| 2007/0027367 A1 | 2/2007 | Oliver et al. |
| 2007/0032733 A1 | 2/2007 | Burton |
| 2007/0213620 A1 | 9/2007 | Reisfeld |
| 2007/0296571 A1 | 12/2007 | Kolen |
| 2008/0001735 A1 | 1/2008 | Tran |
| 2008/0157956 A1 | 7/2008 | Radivojevic et al. |
| 2008/0234568 A1 | 9/2008 | Ouchi |
| 2008/0238757 A1 | 10/2008 | Lin et al. |
| 2008/0269589 A1 | 10/2008 | Thijs et al. |
| 2009/0256739 A1 | 10/2009 | Teshirogi et al. |
| 2010/0049008 A1 | 2/2010 | Doherty et al. |
| 2010/0099954 A1 | 4/2010 | Dickinson et al. |
| 2011/0015495 A1 | 1/2011 | Dothie et al. |
| 2011/0112425 A1 | 5/2011 | Muhlsteff et al. |
| 2012/0245479 A1 | 9/2012 | Ganesh et al. |
| 2013/0006124 A1 | 1/2013 | Eyal et al. |
| 2013/0053653 A1 | 2/2013 | Cuddihy et al. |
| 2013/0135137 A1 | 5/2013 | Mulder et al. |
| 2013/0172770 A1 | 7/2013 | Muehlsteff |

FOREIGN PATENT DOCUMENTS

| | | |
|---|---|---|
| CN | 1860987 A | 11/2006 |
| CN | 1897871 A | 1/2007 |
| JP | 2000083927 A | 3/2000 |
| JP | 2004252770 A | 9/2004 |
| JP | 2005270570 A | 10/2005 |
| JP | 2007-098138 | 4/2007 |
| JP | 2008-071263 | 3/2008 |
| JP | 2008-506423 | 3/2008 |
| KR | 1020040019380 | 3/2004 |
| WO | 01045014 A1 | 6/2001 |
| WO | 2004114193 A2 | 12/2004 |
| WO | 2005055824 A1 | 6/2005 |
| WO | 2005081170 A2 | 9/2005 |
| WO | 2006054306 A2 | 5/2006 |
| WO | 2006090371 A2 | 8/2006 |
| WO | 2007052108 A2 | 5/2007 |
| WO | 2007117719 A2 | 10/2007 |
| WO | 2007143535 A2 | 12/2007 |
| WO | WO-2007143535 A2 * | 12/2007 ........... A61B 5/0507 |
| WO | 2008037020 A1 | 4/2008 |
| WO | 2008057883 A2 | 5/2008 |
| WO | 2008096307 A1 | 8/2008 |
| WO | 2009124297 A1 | 10/2009 |
| WO | 2010048310 A1 | 4/2010 |
| WO | 2010132850 A1 | 11/2010 |
| WO | 2012073183 A1 | 6/2012 |
| WO | 2013093712 A1 | 6/2013 |

OTHER PUBLICATIONS

Fox, Niall A., et al. "An evaluation of a non-contact biomotion sensor with actimetry." 2007 29th Annual International Conference of the IEEE Engineering in Medicine and Biology Society. IEEE, 2007.*

International Search Report and Written Opinion for Application No. PCT/US2009/058020 dated Dec. 2, 2009 (11 pages).

International Preliminary Report on Patentability for PCT International Patent Application No. PCT/US2009/058020, dated Aug. 31, 2010.

"The Fundamentals of FFT-Based Signal Analysis and Measurement in LabVIEW and LabWindows/CVI" National Instruments, Published Jun. 8, 2009. 12 pages. Accessed Jan. 26, 2012. URL: http://zone/ni.com/devzone/cda/tut/p/id/4278#toc0.

Japanese Office Action dated Oct. 18, 2011 of Japanese Applicatikon No. 2009-513469 filed Jan. 30, 2009 (4 pages).

Second Office Action dated Apr. 14, 2011 of Chinese Application No. 200780026740.0 filed Jan. 14, 2009 (16 pages).

European Search Report and Search Opinion for European Patent Application No. 07784266.4, dated Oct. 7, 2010.

Droitcour et al., "Range Correlation and I/Q Performance Benefits in Single-Chip Silicon Doppler Radars for Noncontact Cardiopulmonary Monitoring", IEEE Transactions on Microwave Theory and Techniques, Mar. 3, 2004, vol. 52, No. 3, pp. 838-848.

International Search Report and Written Opinion of the International Searching Authority for PCT International Application No. PCT/US2007/083155, dated Mar. 20, 2008.

Intenational Search Report for PCT International Application No. PCT/US2007/070196, dated Feb. 22, 2008.

International Preliminay Report on Patentability for PCT International Application No. PCT/US2007/070196, dated Dec. 3, 2008.

Japanese Office Action for Application No. 2009-513469 dated May 1, 2012.

U.S. Office Action for U.S. Appl. No. 12/302,704 dated Spetember 16, 2012.

Australian Examination Report for Application No. 2007256872 dated Mar. 20, 2012.

Japanese Office Action for Application No. 2009-513469 dated Nov. 27, 2012.

Chinese Office Action for Application No. 2009801466909 dated Mar. 28, 2013.

Japanese Office Action for Application No. 2011-528091 dated Jul. 16, 2013.

Japanese Decision of Rejection for Application No. 2011-528091 dated Dec. 3, 2013.

Chinese Office Action for Application No. 200980146690.9 dated Feb. 17, 2014.

Australian Examination Report for Application No. 2009296732 dated Oct. 9, 2014.

(56) References Cited

OTHER PUBLICATIONS

Chinese Office Action (Third) for Application No. 200980146690.9 dated Sep. 3, 2014.
Japanese Office Action for Application No. 2011-528091 dated Mar. 3, 2015.
Korean Office Action for Application No. 10-2011-7008451 dated Feb. 29, 2016.
Chinese Office Action for Application No. 200980146690.9 dated May 26, 2016.
Australian Office Action for Application No. 2016204801dated Jul. 15, 2016.
Boric-Lubecke et al., "Range Correlation Effect on ISM band I/Q CMOS Radar for Non-Contact Vital Signs Sensing", IEEE MTT-S Digest, 2003, p. 1945-1948.
Boric-Lubecke et al., "Range correlation and I/Q performance benefits in single-chip silicon doppler radars for noncontact cardiopulmonary monitoring", IEEE Transactions on Microwave Theory and Techniques, vol. 52, No. 3, Mar. 2004, p. 838-848.
P. de Chazal, E. O'Hare, N. Fox, C. Heneghan, "Assessment of Sleep/Wake Patterns Using a Non-Contact Biomotion Sensor", Proc. 30th IEEE EMBS Conference, Aug. 2008, published by the IEEE.
Non-Final Office Action issued in corresponding U.S. Appl. No. 12/565,371 dated Jan. 28, 2019.
Chinese Office Action issued in corresponding CN application No. 201710367770.3 dated Mar. 5, 2020.

\* cited by examiner

SYSTEMS AND METHODS FOR MONITORING QUALITY OF LIFE PARAMETERS USING NON-CONTACT SENSORS

CROSS-REFERENCE TO RELATED APPLICATIONS

The present application is a continuation of U.S. patent application Ser. No. 13/120,640, now U.S. Pat. No. 9,223,935, filed Mar. 23, 2011, which claims benefit to PCT/US2009/058020 filed Sep. 23, 2009, which claims benefit of U.S. Provisional Application 61/099,792 filed Sep. 24, 2008, the disclosures of which are incorporated herein by reference.

BACKGROUND OF THE INVENTION

This disclosure relates to the measurement, aggregation and analysis of data collected using non-contact or minimal-contact sensors together with a means for capturing subjective responses to provide quality of life parameters for individual subjects, particularly in the context of a controlled trial of interventions on human subjects (e.g., a clinical trial of a drug, or an evaluation of a consumer item such as a fragrance).

Monitoring of quality-of-life (QOL) parameters can be of importance when developing interventions aimed at improving a person's QOL. Quality-of-life parameters are measurements of general well-being which are generally accepted as being meaningful to an individual's perception of their life. In general QOL markers have a combination of an underlying objectively measurable elements, and a subjectively related element. Specific non-limiting examples include:

Sleep quality—an individual can subjectively report whether they are sleeping well or badly, and this has an impact on their perceived QOL. For a sleep quality QOL parameter, an objective measurement could be sleep duration, and a subjective input could be "how restful" the sleep was.

Stress—an individual can report on whether they find their current life circumstances to be stressful. For a stress QOL parameter, an objective measurement could be heart rate or cortisol levels; a subjective element could be a stress level questionnaire Relaxation—an individual can report the subjective sensation of being relaxed, which can also be objectively related to autonomic nervous system activity.

Pain—an individual can subjectively record levels of pain using a Pain Index [such as the Visual Analog Scale]. More objective measurements of pain can be obtained using a dolorimeter.

Body temperature—subjects can often report feelings of overheating or coolness which are not directly related to objective measurement of body core temperature.

Vigilance/drowsiness—vigilance, or attentiveness can also be measured objectively (e.g., using the psycho-motor vigilance test) or through subjective questionnaires.

For clarification, a non-contact (or contactless) sensor is one which senses a parameter of a subject's physiology or behavior without any direct physical contact with a subject. Non-limiting examples include a movement detector based on radio-wave reflections, a microphone placed remotely from a subject, an infrared camera recording the surface temperature, or a faucet-monitor which records turning on of a faucet to wash hands. A minimal contact sensor may be considered to be one in which there is some physical contact with a sensor, but this is limited to short durations. Examples include a weight scale, a blood pressure monitor, a breath analyzer, or a hand-held surface ECG monitor. These minimal contact sensors can be distinguished from contact sensors typically used in clinical trials such as ECG patches, oximeters, EEG electrodes, etc, where there typically is adhesion to the body, and typically the sensor is intended for use over prolonged periods of time (e.g. >1 hour).

A key unifying factor in defining QOL parameters is the need to combine objective data from sensors, and subjective data from the monitored subject to assess the overall QOL. A particular challenge then arises when one wishes to measure the impact of an intervention on changes in QOL. For example, a company who has developed a drug to counteract sleep disruption will be interested to see if its drug has had any direct impact on a person's sleep which has resulted in either objectively or subjectively improved QOL. Similarly if a company has developed a product such as a skin emollient to reduce itchiness due to dry skin, they may wish to see if there has been an improved QOL (i.e., reduced scratching, lower level of discomfort) etc.

One commonly accepted means for answering such questions is to conduct a clinical or consumer trial which poses a statistical hypothesis which can be verified or rejected with a certain level of confidence. For example, in drug trials a double-blinded random controlled trial is a well accepted methodology for ascertaining the effect of drugs. However, measurement of QOL is difficult to conduct for a number of reasons, which various aspects of this disclosure can overcome: (a) it can be difficult to define a suitable measure for a QOL outcome, (b) by wearing a measurement device to measure QOL, one may directly impact on the exact quality-of-life parameter you wish to study, (c) there are logistical and financial challenges of measuring parameters in a natural "home" setting rather than in a formal laboratory setting. There are a variety of conventional techniques to measure some aspects of QOL which will now be discussed, together with their limitations.

Monitoring of a quality-of-life parameter can be motivated by a desire to integrate it into an intervention program. As an example, a person may undertake cognitive behavioral therapy (CBT) to reduce their stress-related quality of life. An important component of a CBT program is the ongoing assessment of the stress quality of life index, whose measurement will itself form part of the behavioral intervention. As a second example of an embodiment of the disclosure, we will describe a system for improving sleep quality through use of objective and subjective measurements of sleep quality-of-life indices.

As specific examples of the limitations of the current state of the art, consider the problem of measuring sleep quality in response to an anti-insomnia drug. Firstly, defining "sleep quality" as it relates to quality of life can be difficult, as this will often be a combination of objective and subjective measurements. Secondly, the current method favored for measuring sleep is to use a so-called polysomnogram which measures multiple physiological parameters (EEG, ECG, EOG, respiratory effort, oxygen level etc.). While the resulting physiological measurements are very rich, their measurement fundamentally alters the sleeping state of the subject (e.g., it is harder for them to turn over in bed), and cannot represent a true QOL sleep measurement. Finally, the current cost of the polysomnogram test (approximately $1500 in 2008) makes it an impractical tool for measurement of sleep quality in large numbers of subjects over long periods of time. Accordingly, there is a need for a system which can provide robust measurements of sleep quality-of-life in a highly non-invasive fashion. In an embodiment of our system, we describe one method for objectively measuring sleep quality using a totally non-invasive biomotion sensor. This can be combined with a number of subjective tools for measuring sleep quality, such as the Pittsburgh Sleep Quality Index and the Insomnia Severity Index (these consist of questionnaires on sleep habits such as time-to-bed, estimated time-to-fall-asleep etc.

Another QOL parameter of interest is stress level or, conversely, relaxation. Current techniques for objective measurement of stress include measurement of heart rate variability or cortisol levels. However, measurement of heart rate variability typically requires the subject to wear electrodes on the chest, which is often impractical for situations of daily living. Likewise, collection of cortisol samples to assess stress requires frequent collection of saliva samples, and is difficult to integrate into a daily living routine. There are also a number of widely used subjective measurements of stress or anxiety (e.g., Spielberger's State-Trait Anxiety Inventory). Accordingly, a method, system or apparatus which can reliably gather information about stress-related QOL parameters would have utility in a variety of settings.

Finally, measurement of the quality-of-life implications of chronic pain (such as chronic lower back pain) would have utility for assessing the benefit of therapies, or for providing cognitive feedback on pain management. Current subjective measurement tools such as the Oswestry Disability Index and the 36-Item Short-Form Health Survey are used to assess subjective quality of life in subjects with chronic pain conditions. Objective measurements of pain are not well defined, but there is some evidence that heart rate is correlated with pain intensity.

Accordingly, there is a clearly established need for systems and methods which measure quality-of-life outcomes in ambulatory/home settings, and which have minimal impact on the daily routine of the person whose QOL is being monitored. This is a particular need in clinical trials for non-contact or minimal contact sensors where the effects of interventions such as drugs, ointments, physiotherapy, nutriceuticals, behavior changes etc. are being evaluated.

SUMMARY

This disclosure provides various embodiments of an apparatus, system, and method for monitoring of quality-of-life parameters of a subject, using contact-free or minimal-contact sensors, in a convenient and low-cost fashion. The typical user of the system is a remote observer who wishes to monitor the QOL of the monitored subject in as non-invasive fashion as possible. The system typically includes: (a) one or more contactless or minimal-contact sensor units suitable for being placed close to where the subject is present (e.g., on a bedside table), (b) an input device for electronically capturing subjective responses such as a cell-phone, PDA etc., (c) a device for aggregating data together and transmitting to a remote location, (d) a display unit for showing information to the local user, and (e) a data archiving and analysis system for display and analysis of the quality-of-life parameters. The component (e) can also be used as a feedback device for interventional programs. For convenience, the sensor unit, input unit, data aggregation/transmission unit, and the display/monitoring unit can be incorporated into a single stand-alone unit, if desired (for example, all of these functions could be integrated on a cell-phone platform). The sensor units may include one or more of a non-contact measurement sensor (for detection of parameters such as sound, general bodily movement, respiration, heart rate, position, temperature), and one or more minimal contact sensors (e.g. weighing scales, thermometer). In one or more aspects of this disclosure, a system may incorporate a processing capability (which can be either at the local or remote sites) to generate quality-of-life parameters based on the objective and subjective measurements from a user. As a specific example, an overall sleep quality-of-life could be generated by combining the subjective response of the user to the Insomnia Severity Index together with an objective measurement of sleep duration.

In one or more embodiments, the disclosed approaches (pharmaceutical, device-based or behavioral) are useful in improving the quality-of-life parameters for these subjects. In particular, non-contact or minimal-contact measurement of quality-of-life parameters such as sleep, stress, relaxation, drowsiness, temperature and emotional state of humans is disclosed, together with means for automated sampling, storage, and transmission to a remote data analysis center. In one or more embodiments, one aspect of the system measures objective data with as little disruption as possible to the normal behavior of the subject.

In one particular embodiment, a quality-of-life monitoring system for human subjects, includes a plurality of multi-parameter physiological and environmental sensors configured to detect a plurality of physiological and environmental parameters related to a quality of life assessment, wherein each of said plurality of sensors either have no contact or minimal contact with a monitored subject; a timer that controls sampling of the detected parameters and allows a chronological reconstruction of recorded signals relating thereto; an input device which captures subjective responses from the monitored subject; a data storage device configured to record sampled signals; a data transmission capability so that data collected from a subject can be transmitted to a remote data monitoring center, and messages can be transmitted to the monitoring sensors; and a data monitoring and analysis capability so that overall quality-of-life parameters can be calculated based on the measured signals.

In another embodiment, a method for assessing a quality of life index includes measuring multi-parameter physiological and environmental parameters which are related to a quality of life assessment of a monitored subject with no contact or minimal contact with the monitored subject; collecting subjective responses from the monitored subject about their quality-of-life; analyzing objective and subjective measurements to generate a quantitative quality-of-life index; and generating suggested interventions to affect the measured quality of life index of the monitored subject.

BRIEF DESCRIPTION OF THE DRAWINGS

Embodiments of the disclosure will now be described with reference to the accompanying drawings in which.

DETAILED DESCRIPTION

Figure 1:
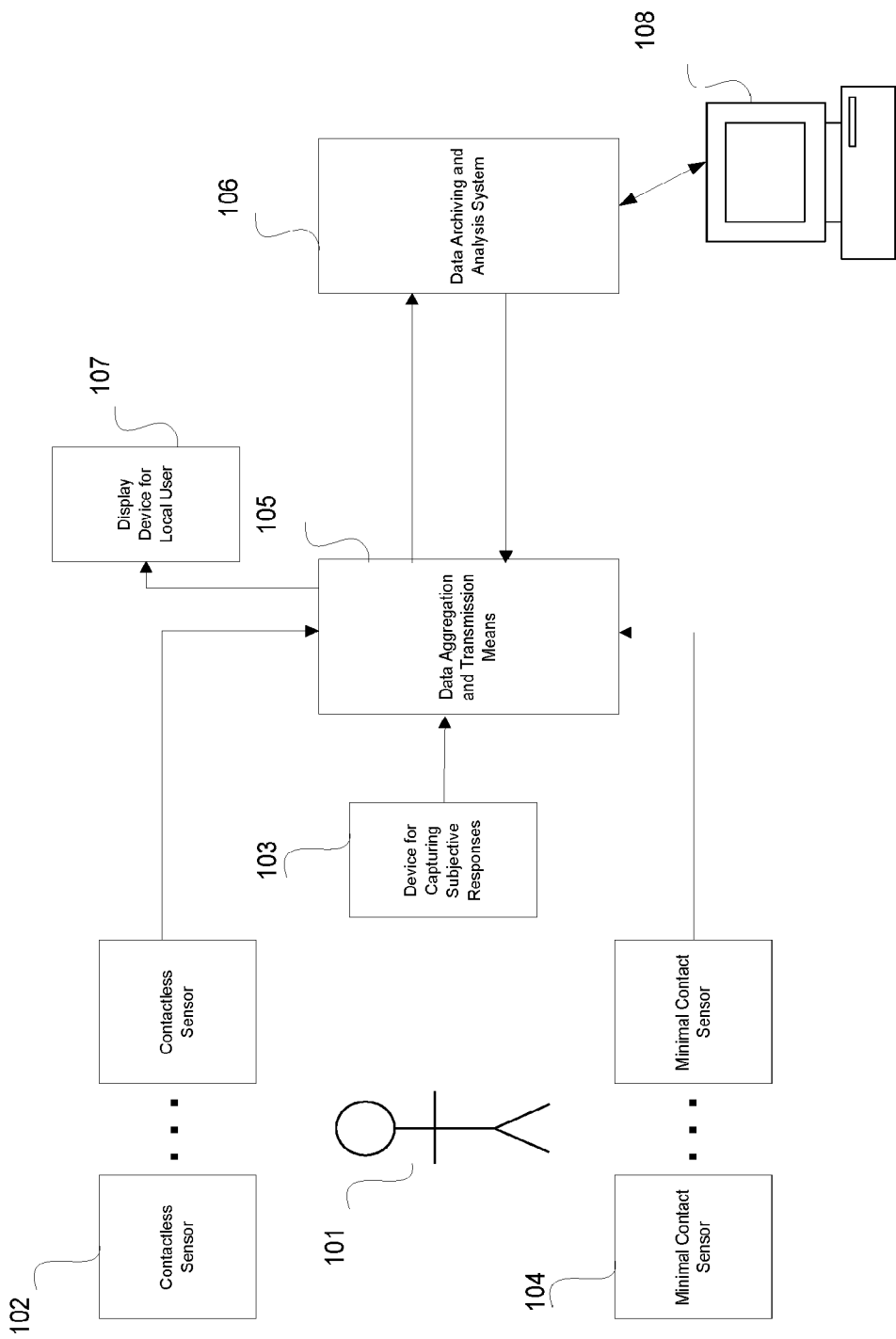
FIG. 1 is a diagram illustrating an overall schematic of an embodiment.

FIG. 1 is a diagram illustrating an overall schematic of an embodiment of this disclosure. Monitored subject 101 may be observed by a plurality of contactless 102 and minimal contact sensors 103. Subject 101 may also has access to input device 104 capable of obtaining subjective feedback from the subject through written text or recorded sound. Data aggregation and transmission device 105 collects the data from the sensors 102, 103 and 104, and may also control data sampling and input parameters used by the various sensors and devices. Optionally, display/feedback device 107 can be provided to the local user (e.g., this might indicate whether a signal is being collected from them, or give feedback on the most recent set of QOL parameters measured). Data aggregation and transmission device 105 may be configured to communicate in a bilateral way with remote data archiving and analysis system 106. Data archiving and analysis system 106 may store data from a plurality of subjects, and can carry out analysis of the recorded signals and feedback. It may also communicate with data display device 107 which can show the results of the analysis to a user, or with an optional separate display device 108 which shows the QOL parameters to a remote user.

Figure 2:
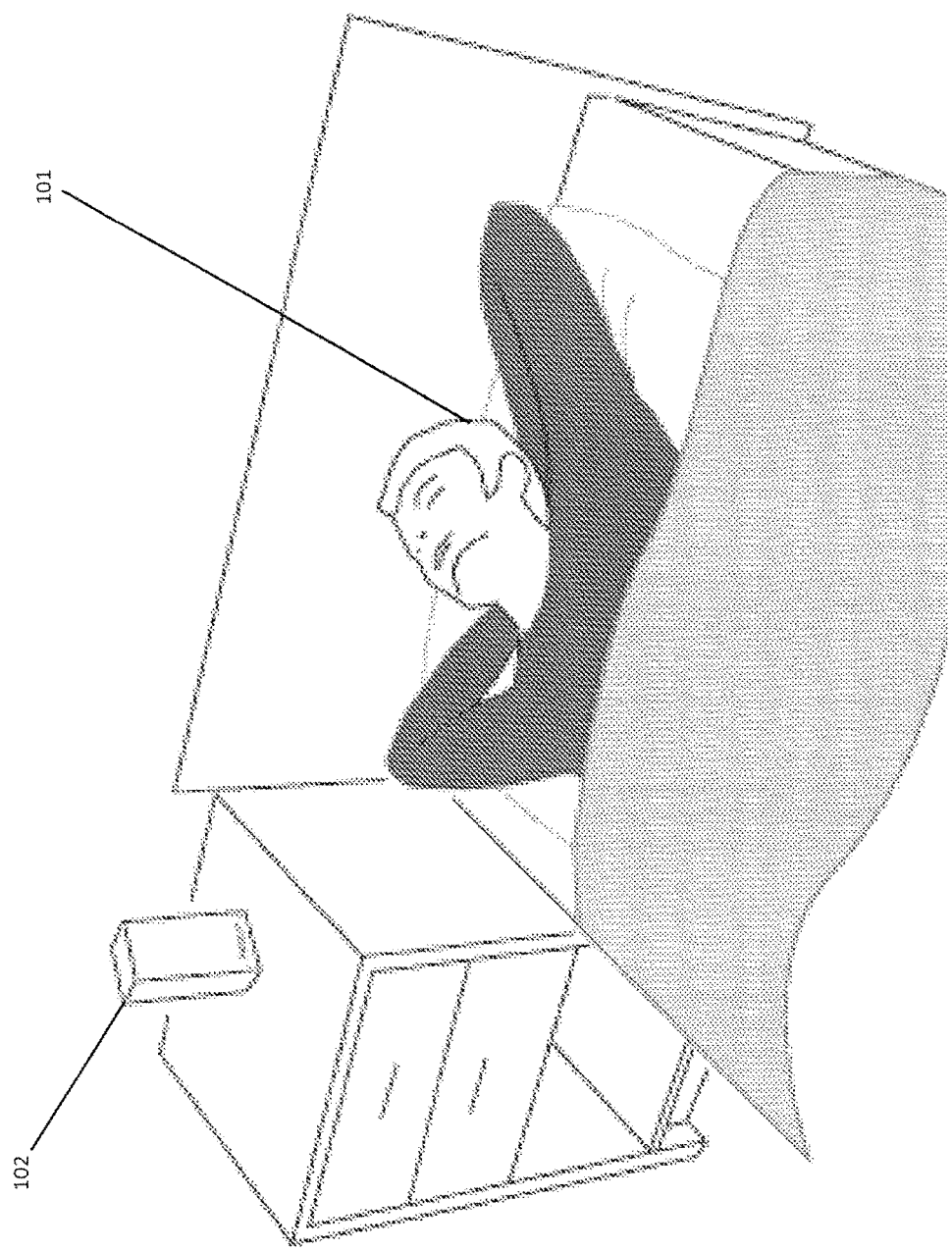
FIG. 2 is a specific example of an embodiment in which a contactless sensor is used to monitor the sleeping state of a subject, by placement in a nearby location (bedside locker)

FIG. 2 illustrates an embodiment of a contactless sensor that objectively monitors the sleeping state of a subject. In this embodiment, the sensor unit may contain one or more of a radio-frequency based biomotion sensor, a microphone (to pick up ambient sound), a temperature sensor (to pick up ambient temperature), a light sensor (to pick up ambient light levels), and an infrared detector for measuring the subject temperature. The contactless sensor may be placed on a bedside table, for example.

Figure 3:
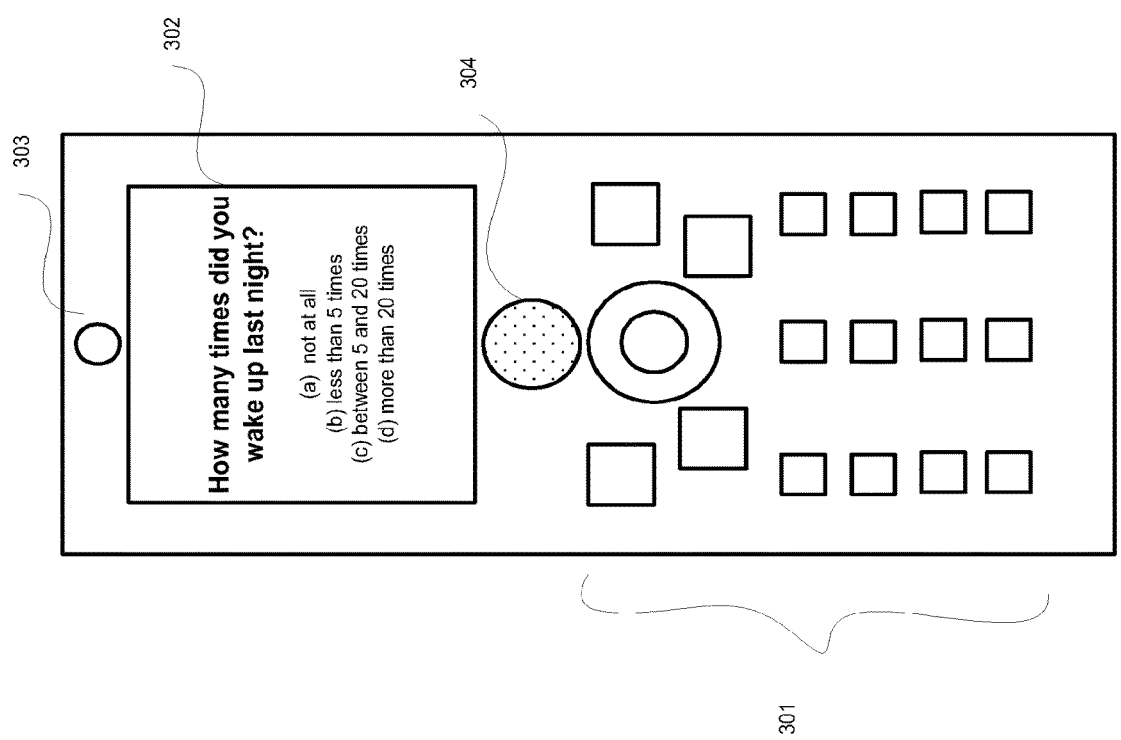
FIG. 3 is an example of an input device embodiment that could be used to capture subjective responses from individuals.

FIG. 3 illustrates an example of an embodiment of an input device for collecting user input. The input device would typically include alphanumeric keypad 301, display 302, microphone 303, and loudspeaker 304. This allows the generation of questions using either visual or audio means, and a person can then answer the questions using either text or audio input.

Figure 4:
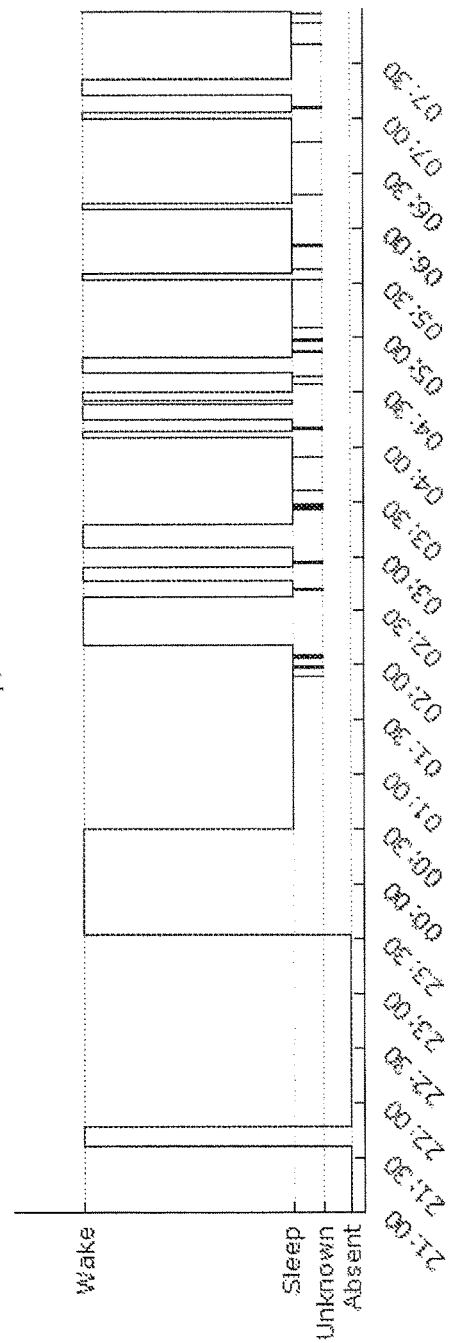
FIG. 4 is an alternative example of an embodiment in which a web-site could be used to capture the subjective responses from an individual.

FIG. 4 illustrates an embodiment using a personal computer with an internet browser to capture subjective perceptions of sleep.

Figure 5A:
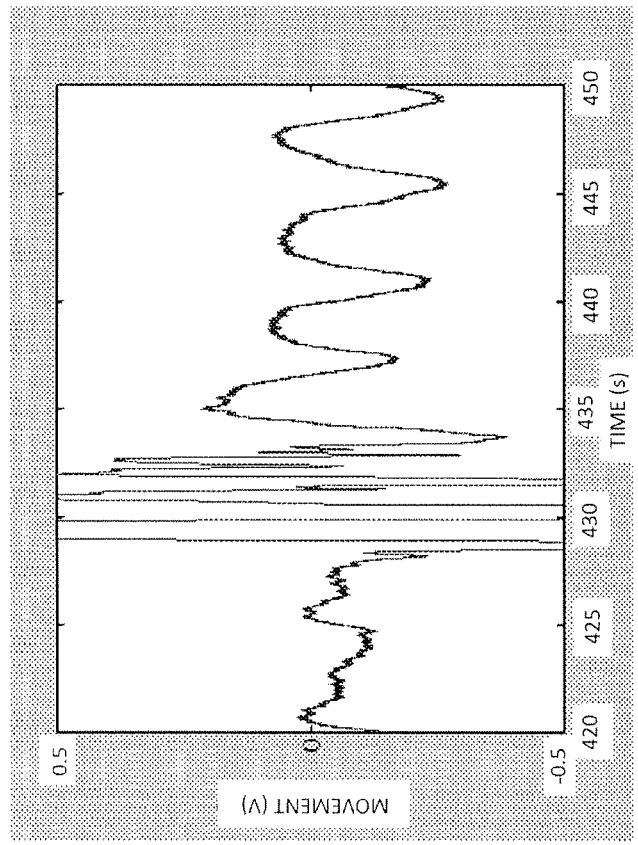
FIGS. 5A and B show representations of some of the raw data captured by a specific contactless sensor used in a sleep trial based on an embodiment of this disclosure.
Figure 5B:
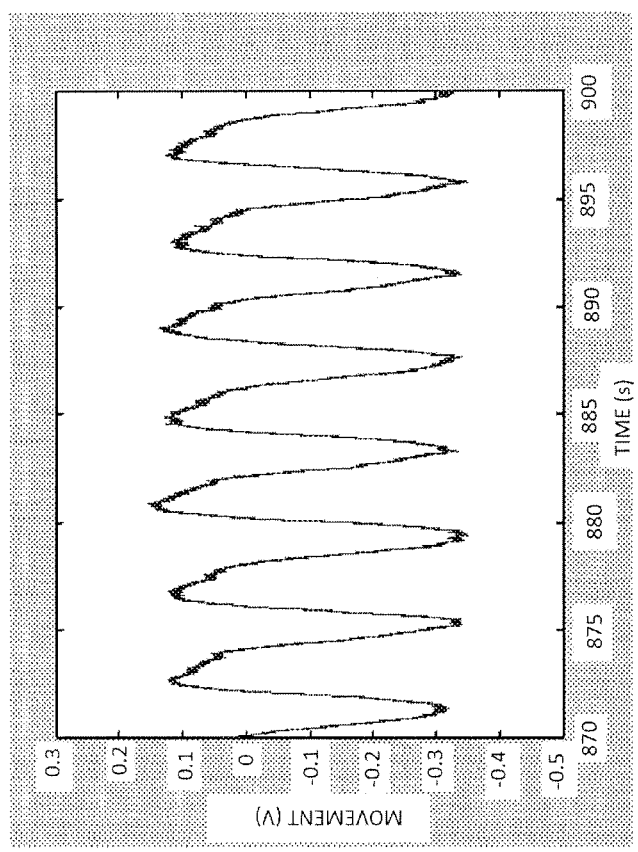

FIGS. 5A and 5B provide examples of raw signals captured using a contactless sensor in a trial for measuring sleep quality-of-life. FIG. 5A shows the signal when a person is asleep and then turns over on their side. FIG. 5B shows the signal when the person is in deep sleep.

Figure 6:
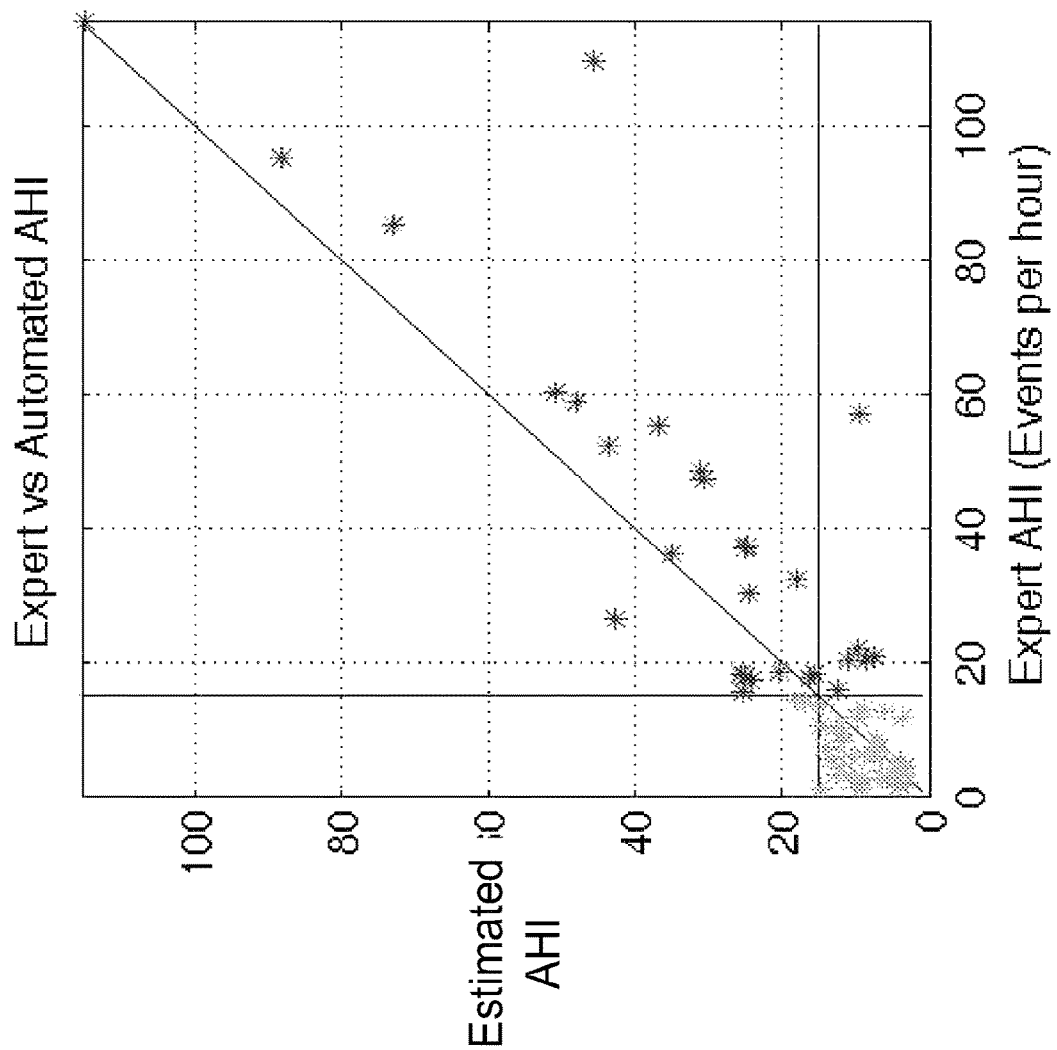
FIG. 6 shows example results of the system in measuring sleep apnea in clinical trial.

FIG. 6 is an example of how the contactless system can estimate apnea-hypopnea index in a clinical trial with an accuracy similar to that of the current polysomnogram (PSG) estimates.

Figure 7A:
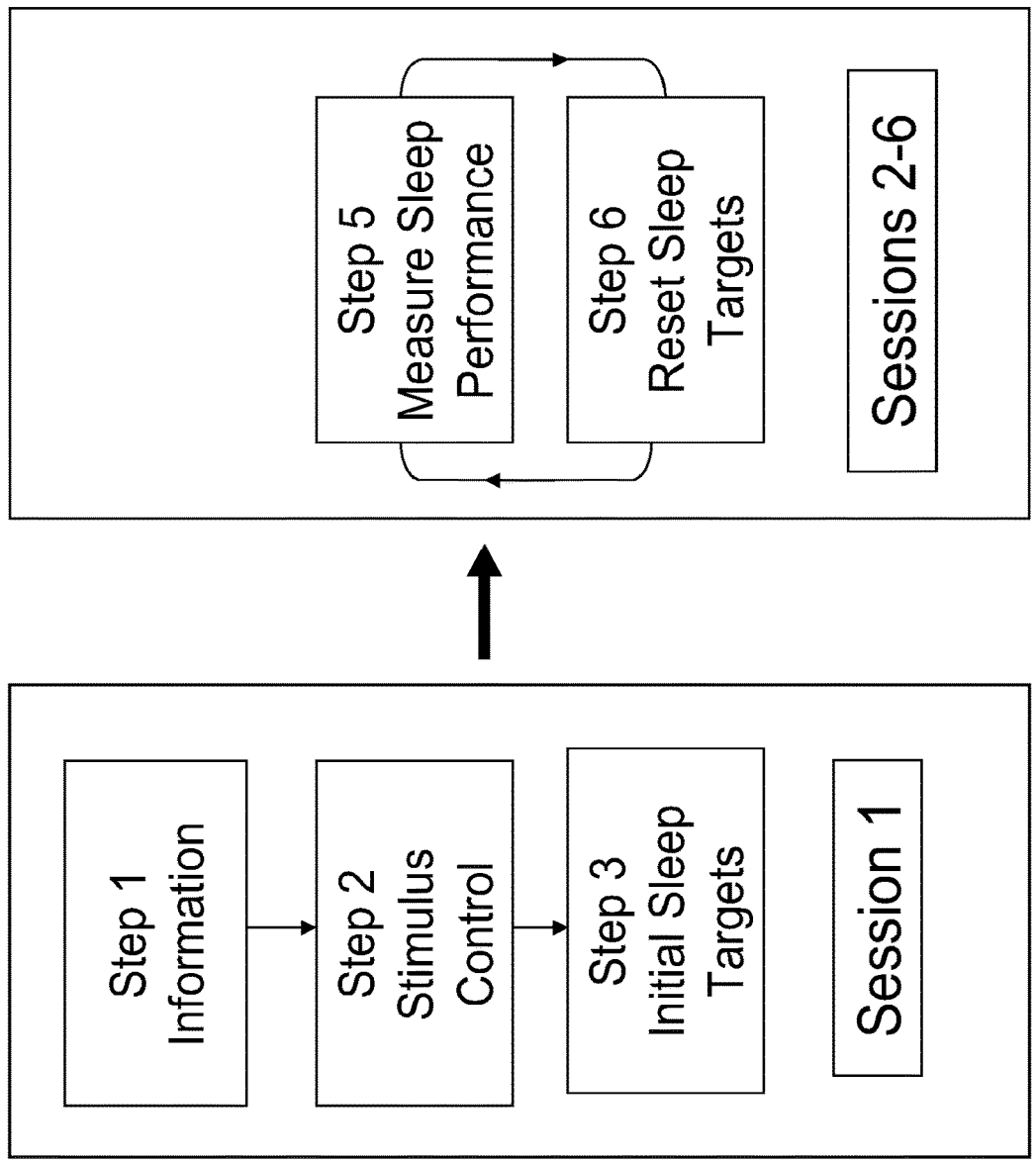
FIGS. 7A and 7B show schematic representations of behavioral interventions based on one or more embodiments of this disclosure.

FIG. 7 is an example of a behavioral intervention based on use of the system to enhance sleep quality. FIG. 7(A) shows the components of a intervention based over several weeks, in which there is an initial session at which detailed information about sleep is provided, and the person is given the system for measurement of their sleep quality-of-life index (SQOLI).

Figure 7B:
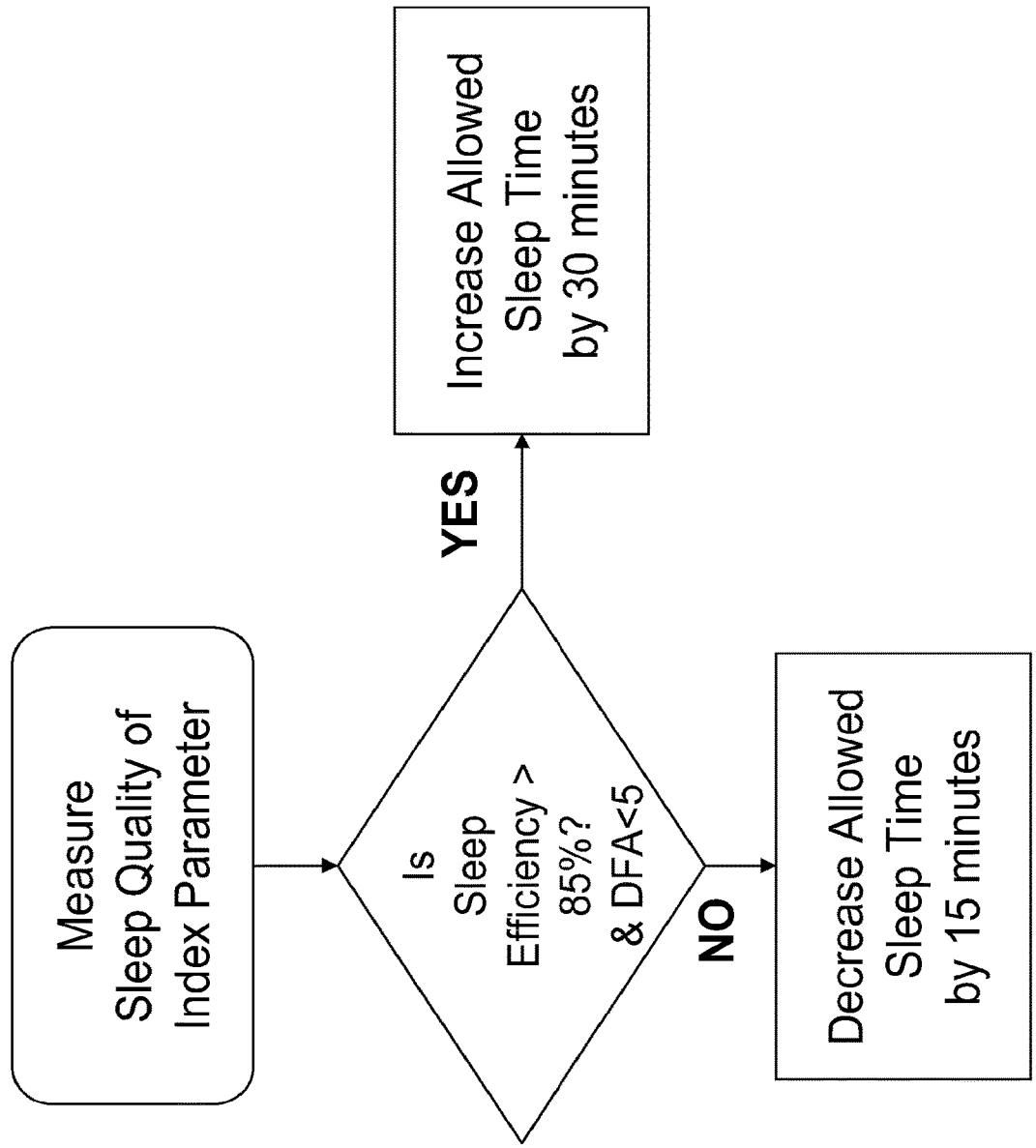

FIG. 7(B) shows an example of a specific algorithm that could be used within the intervention, based on the feedback from the SQOLI monitoring. For example, if they achieve an SQOLI greater than target, they can increase their time in bed by 30 minutes. If they fail, they can reduce time in bed by 15 minutes.

A typical embodiment of a system of this disclosure may include one or more non-contact sensors or minimal-contact sensors that can include one or more of the following:

(a) A biomotion sensor which measures movement, and which derives respiration, heart rate and movement parameters. An example of such a sensor is more fully described in the article written by P. de Chazal, E. O'Hare, N. Fox, C. Heneghan, "Assessment of Sleep/Wake Patterns Using a Non-Contact Biomotion Sensor", Proc. 30th IEEE EMBS Conference, August 2008, published by the IEEE, the entire contents of which are incorporated herein by reference. In one embodiment, the biomotion sensor may use a series of radio-frequency pulses at 5.8 GHz to generate echoes from a sleeping subject. The echoes may be mixed with the transmitted signals to generate a movement trace which includes movements due to breathing, heart rate, and positional changes.

(b) An audio sensor which measures ambient sound. A specific example of a microphone appropriate for inclusion in the system would be the HK-Sound Omni, −27 dB microphone with part number S-0M9765C273S-C08.

(c) A temperature sensor which measures environmental temperature (typically to ±1C). A specific example of a temperature sensor appropriate for inclusion would be the National Semiconductor LM20, SC70 package.

(d) A light level sensor would measure light level. A specific example of a light level sensor appropriate for inclusion is the Square n·.·E• Clipsal Light-Level Sensor.

(e) A body-temperature measuring sensor. A specific example of a sensor that may be used in the system is the body thermometer Part No. 310 from the YuanYa Far Asia Company.

The minimal contact sensors may include one or more of the following:

(a) A weighing scales for measuring body weight. A specific RST 3.3-005 CONexample is the A&D UC-321PBT.

(b) A blood pressure device, such as the A&F UA767PBT.

(c) A continuous positive airway pressure device for treating sleep apnea, such as the ResMed Autoset Spirit S8.

(d) A pedometer for measuring step-counts (such as the Omron Pocket Pedometer with PC software, HJ-7201TC).

(e) A body-worn accelerometer for measuring physical activity during the day (such as the ActivePAL device).

(f) A body composition analyzer such as the Omron Body Composition Monitor with Scale, HBF-500, which calculates visceral fat and base metabolic rate.

(g) Other contactless or minimally contacting devices could also be included.

In one or more embodiments, the system may include a data-acquisition and processing capability which provides a logging capability for the non-contact and minimal-contact sensors described above. This typically could include, for example, an analog-to-digital converter (ADC), a timer, and a processor. The processor may be configured to control the sampling of the signals, and may also apply any necessary data processing or reduction techniques (e.g., compression) to minimize unnecessary storage or transmission of data.

A data communication subsystem may provide communication capability which could send the recorded data to a remote database for further storage and analysis, and a data analysis system including, for example, a database, can be configured to provide processing functionality as well as input to a visual display.

In one specific embodiment of the system, data acquisition, processing, and communications can utilize using, for example, a Bluetooth-enabled data acquisition device (e.g. the commercially available BlueSentry® device from Roving Networks). Other conventional wireless approaches may also be used. This provides the ability to sample arbitrary voltage waveforms, and can also accept data in digital format.

In this embodiment, the Bluetooth device can then transmit data to a cell phone using the Bluetooth protocol, so that the data can be stored on a cell-phone memory. The cell phone can also carry out initial processing of the data. The cell phone can also be used as a device for capturing subjective data from the user, using either a text-based entry system, or through a voice enabled question-and-answer system. Subjective data can also be captured using a webpage.

The cell phone can provide the data transmission capability to a remote site using protocols such as GPRS or EDGE. The data analysis system is a personal computer running a database (e.g., the My SQL database software), which is capable of being queries by analysis software which can calculate useful QOL parameters. Finally a data display capability can be provided by a program querying the database, the outputs of the analytical program and using graphical or text output on a web browser.

As an example of the clinical use of a specific embodiment, the system was used to measure quality-of-life related to sleep in a specific clinical trial scenario. A group of 15 patients with chronic lower back pain (CLBP), and an age and gender matched cohort of 15 subjects with no back pain were recruited. After initial screening and enrollment, study participants completed a baseline assessment. Gender, age, weight, height, BMI and medication usage were recorded. All subjects completed baseline self report measures of sleep quality (Pittsburgh Sleep Quality Index Insomnia Severity Index [16], quality of life (SF36v2) [17] and pain as part of the SF36v2 questionnaire (bodily pain scale of the SF36v2). The CLBP subjects also completed the Oswestry Disability Index (ODI) as a measure of functional disability related to their low back pain. All subjects then underwent two consecutive nights of objective monitoring using the non-contact biomotion sensor mentioned above, while simultaneously completing a subjective daily sleep log; the Pittsburgh Sleep Diary. Table 1 shows some objective measurements of sleep using the system, and includes the total sleep time, sleep efficiency, sleep onset latency. Other objective parameters which could be measured would include: number of awakenings (>1 minute in duration) and wake-after-sleep-onset.

TABLE 1

Objective sleep indices obtained using the system

| Variable | Control Group (mean ± sd) | CLBP Group (mean ± sd) | p-value |
|---|---|---|---|
| Total sleep time (mins) | 399 (41) | 382 (74) | 0.428 |
| Sleep Efficiency (%) | 85.8 (4.4) | 77.8 (7.8) | 0.002 |
| Sleep Latency (mins) | 9.4 (10.2) | 9.3 (11.1) | 0.972 |

The objective sleep indices described in Table 1 were obtained using a sleep stage classification system that processed the non-contact biomotion sensor data to produce sleep and awake classifications every 30 seconds. This was developed using the following observations:

Large movements (e.g., several cm in size) can be easily recognized in the non-contact signal. Bodily movement provides significant information about the sleep state of a subject, and has been widely used in actigraphy to determine sleep/wake state. The variability of respiration changes significantly with sleep stage. In deep sleep, it has long been noted that respiration is steadier in both frequency and amplitude than during wakefulness of REM sleep.

Accordingly, a first stage in processing of the non-contact biomotion signal was to identify movement and respiration information. To illustrate how this is possible, FIG. 5A shows an example of the signal recorded by the non-contact sensor when there is a significant movement of the torso and arms due to the person shifting sleeping position. An algorithm based on detection of high amplitude and frequency sections of the signal was used to isolate the periods of movement.

For periods where there is no significant limb or torso movement, respiratory-related movement is the predominant recorded signal and estimates of breathing rate and relative amplitude are obtained using a peak and trough identifying algorithm. FIG. 5B illustrates the signal recorded by the sensor during a period of Stage 4 sleep that demonstrates a steady breathing effort.

To validate the performance of the system in correctly labeling 30-second epochs, we recorded signals simultaneously with a full polysomnogram (PSG) montage. We compared the sleep epoch annotations from the PSG and the non-contact biomotion sensor and report the overall classification accuracy, sleep sensitivity and predictivity, wake specificity and predictivity. The overall accuracy is the percentage of total epochs correctly classified. The results are shown in Table 2, and provide evidence that the system can objectively measure sleep with a high degree of accuracy.

TABLE 2

Accuracy of objective recognition of sleep state using the contactless method

| Overall | | By sleep state | |
|---|---|---|---|
| Awake | 69% | Awake | 69% |
| Sleep | 87% | REM | 82% |
| Pred. of Awake | 53% | Stage 1 | 61% |
| Pred. of Sleep | 91% | Stage 2 | 87% |
| Accuracy | 82% | Stage 3 | 97% |
| | | Stage 4 | 98% |

Table 3 shows some of the subjective measurements from the same subjects, and includes their subjective assessment of sleep duration, sleep efficiency, number of awakenings, and sleep latency for each night, as well as their overall PSQI and 1SI scores.

TABLE 3

Subjective sleep indices obtained using the system

| Variable | Control Group (mean ± sd) | CLBP Group (mean ± sd) | p-value |
|---|---|---|---|
| Pittsburgh Sleep Quality Index | 2.1 (2.1) | 11.7 (4.3) | <0.001 |
| Insomnia Severity Index | 2.8 (4.6) | 13.4 (7.3) | <0.001 |
| Estimated Sleep Onset Latency | 11.7 (4.3) | 45.3 (27.7) | <0.001 |
| Estimated Sleep Efficiency | 95.3 (5.8) | 73.4 (16.5) | <0.001 |
| Estimated Night Time Awakenings | 2/15 | 15/ | <0.001 |

The system can report these subjective and objective measurements of sleep but, in one aspect, it can also report parameters related to overall Sleep Quality of Life Index (SQOLI) which combines objective and subjective measurements. There are a number of ways in which this could be done. For example, we could define the following SQOL indices:

SQOL duration={0.8×OBJECTIVE SLEEP DURATION+0.2×SUBJECTIVE SLEEP DURATION}

SQOL fragmentation={(number of periods of objectively measured wakefulness>1 minute+reported self awakenings)/objective sleep duration}

$$SQOL\ latency = \sqrt{OBJECTIVE\ SLEEP\ LATENCY \times SUBJECTIVE\ SLEEP\ LATENCY}$$

The skilled user will be able to construct other combined measurements of sleep quality of life which capture the most meaningful outcomes for a particular application.

In another embodiment, the system may be used to capture quality-of-life in patients with chronic cough (e.g., patients suffering from chronic obstructive pulmonary disease). In this embodiment, two contactless sensors may be used: the non-contact biomotion sensor described above, and a microphone. The system can measure objectively sounds associated with each coughing episode, and the respiratory effort associated with each cough. This provides a more accurate means of collecting cough frequency than relying on sound alone. There are also subjective measurements of cough impact on quality of life (e.g., the parent cough-specific QOL (PC-QOL) questionnaire described in "Development of a parent-proxy quality-of-life chronic cough-specific questionnaire: clinical impact vs psychometric evaluations," Newcombe P A, Sheffield J K, Juniper E F, Marchant J M, Halsted R A, Masters I B, Chang A B, Chest. 2008 February; 133(2):386-95).

As another exemplary embodiment, the system could be used as a screening tool to identify sleep apnea severity and incidence in a clinical trial setting. In this embodiment, the contactless biomotion sensor is used to detect periods of no-breathing (apnea) and reduced amplitude breathing (hypopnea). FIG. 6 shows the estimated sleep apnea severity of the patients enrolled in a clinical trial, prior to therapy, as an example of how the system can be used.

The user skilled in the art will realize that the system can be used in a number of clinical trial settings where measurement of quality-of-life is important. As specific examples of such uses, we can consider:

Measurement of sleep quality of life in patients with atopic dermatitis (AD). Subjects with AD often have poor quality of life due to daytime itchiness combined with poor sleep quality due to subconscious scratching during sleep. In a clinical trial designed to assess the impact of an intervention such as a new drug or skin-cream, the system can be used to capture subjective and objective quality of life parameters as a final outcome measure. The outcome of the sleep quality-of-life index measurement can be a recommendation on whether to use a certain active medication, and the dosage of that medication.

Measurement of sleep quality in infants in response to feeding products. For example, lactose intolerance is known to affect quality-of-life in babies due to disrupted sleep, stomach pain, and crying episodes. Feeding products which aim to overcome lactose intolerance can be assessed by combination of objective sleep indices plus parent-reported crying episodes, to form an overall quality-of-life index.

As a further specific embodiment, sleep quality can be enhanced by providing a behavioral feedback program related to sleep quality of life. A person self-reporting insomnia can use the system as follows to enhance their sleep quality of life.

On a first visit with a physician, a person can self-report general dissatisfaction with their sleep quality of life. They can then choose to undertake a cognitive behavioral therapy program in the following steps.

Step 1: They undertake an induction session with a therapist or self-guided manual. In this induction step, the individual is introduced to information about basic physiological mechanisms of sleep such as normal physiological sleep patterns, sleep requirements, etc. This step ensures there are no incorrect perceptions of sleep (i.e. a person believing that 3 hours sleep a night is typical, or that you must sleep exactly 8 hrs per day for normal health).

Step 2: Bootzin stimulus control instructions. In this step, subject-specific information is established, and basic behavioral interventions are agreed. For example, firstly, the subject and therapies agree a target standard wake-up time (e.g., 7 AM). They then agree behavioral interventions such as getting out of bed after 20 minutes of extended awakening, and the need to avoid sleep-incompatible bedroom behavior (e.g., television, computer games, . . . ). They may agree to eliminate daytime naps.

Step 3: Establish initial target. Based on discussions above, the patient and therapist may then agree a sleep quality of life index (SQOLI) which will act as a target. As a specific example, the SQOLI may be based on achieving 85% sleep efficiency and a subjective "difficulty falling asleep" rating of <5 (on a 1-10.scale where 10 is very difficult and 1 is easy) The behavioral program will then consist of a week in which the patient tries to achieve the target based on going to bed 5 hours before the agreed wake-up time (e.g. at 2 AM in our example). The disclosure we have described above in FIGS. 1 to 5 provides the objective measurements of sleep efficiency and combines with the subjective user feedback to produce an SQOLI. At the end of the first week, the patient and therapist review the SQOLI measurements and determine the next step.

Step 4: Feedback loop based on Sleep Quality of Index. If the subject has achieved the desired SQOLI in the first week, then a new target is set. As a specific example, the subject will now go to bed 5.5 hours before the agreed wake up time, but will still try to achieve the same targets of 85% sleep efficiency and "difficulty falling asleep" metric<5. In subsequent weeks, the algorithm will be applied that the person can increase their sleep time by 30 minutes, provided they have met the targets in the previous week. This process can continue until a final desired steady state sleep quality of life index is reached (e.g., sleeping 7.5 hrs per night with a sleep efficiency of >85%).

The person skilled in the art will realize that a number of behavioral interventions have been developed and described in the literature for improving sleep quality. However a limitation of all these current approaches is that they do not have a reliable and easy means for providing the sleep quality of life metric, and it is this limitation which the current disclosure overcomes. Furthermore, the person skilled in the art will also realize that a number of pharmaceutical interventions are appropriate for improvement of sleep quality (e.g. prescription of Ambien®), and that the disclosure described here can support these medical interventions also.

STATEMENT OF INDUSTRIAL APPLICABILITY

The apparatus, system and method of this disclosure finds utility in contactless and minimum contact assessment of quality-of-life indices in clinical and consumer trials, and in interventions to improve the quality of life.

The invention claimed is:

1. A system comprising:
a first non-contact sensor configured to generate first measured data based on transmitted signals emitted towards a subject and received signals reflected from the subject;
one or more processors; and
a non-transitory computer readable storage medium having instructions that, when executed by the one or more processors, cause the one or more processors to:
receive the first measured data;
distinguish periods of the first measured data in which respiratory-related movement is predominant from periods of the first measured data in which bodily movement is predominant based on an amplitude value and a frequency value derived from the first measured data;
obtain respiratory data from the periods of the first measured data in which respiratory-related movement is predominant;
obtain movement data from the periods of the first measured data in which bodily movement is predominant;
calculate a quality of life index based on the respiratory data and the movement data; and
generate feedback based on the calculated quality of life index.

2. The system of claim 1, wherein the generated feedback includes a recommendation to use a medication or a recommended dosage of the medication.

3. The system of claim 1, wherein the generated feedback includes a plurality of instruction steps for the subject to achieve a set target quality of life parameter.

4. The system of claim 3, wherein at least one of the instruction steps includes setting an updated target quality of life parameter based on the calculated quality of life index when the set target quality of life parameter is reached.

5. The system of claim 1, wherein the one or more processors and the non-transitory computer readable storage medium are in a portable handheld device.

6. The system of claim 1, wherein the instructions, when executed by the one or more processors, further cause the one or more processors to prompt the subject to enter subjective data via a user interface, and wherein the quality of life index is calculated based on the respiratory data, the movement data, and the subjective data.

7. The system of claim 6, wherein the subjective data comprises a subjective sleep duration value, a reported number of awakenings, or a subjective sleep latency value.

8. The system of claim 1, wherein obtaining the respiratory data comprises estimating breathing rates and relative amplitudes for the periods of the first measured data in which respiratory-related movement is predominant using a peak and trough identifying algorithm.

9. The system of claim 1 further comprising:
a second non-contact sensor configured to generate second measured data based on sounds associated with one or more coughs of the subject,
wherein the instructions, when executed by the one or more processors, further cause the one or more processors to receive the second measured data, and
wherein the quality of life index is calculated based on the respiratory data, the movement data, and the second measured data.

10. The system of claim 9, wherein the respiratory data includes respiratory effort data associated with the one or more coughs of the subject.

11. A method comprising:
transmitting, with a first non-contact sensor, signals towards a subject;
receiving, with the first non-contact sensor, signals reflected from the subject;
generating, with the first non-contact sensor, first measured data based on the transmitted and received signals;
receiving, with one or more processors, the first measured data;
distinguishing, with the one or more processors, periods of the first measured data in which respiratory-related movement is predominant from periods of the first measured data in which bodily movement is predominant based on an amplitude value and a frequency value derived from the first measured data;
obtaining, with the one or more processors, respiratory data from the periods of the first measured data in which respiratory-related movement is predominant;
obtaining, with the one or more processors, movement data from the periods of the first measured data in which bodily movement is predominant;
calculating, with the one or more processors, a quality of life index based on the respiratory data and the movement data; and
generating, with the one or more processors, feedback based on the calculated quality of life index.

12. The method of claim 11, wherein the generated feedback includes a recommendation to use a medication or a recommended dosage of the medication.

13. The method of claim 11, wherein the generated feedback includes a plurality of instruction steps for the subject to achieve a set target quality of life parameter.

14. The method of claim 13, wherein at least one of the instruction steps includes setting an updated target quality of life parameter based on the calculated quality of life index when the set target quality of life parameter is reached.

15. The method of claim 11 further comprising:
prompting, with the one or more processors, the subject to enter subjective data via a user interface,
wherein the quality of life index is calculated based on the respiratory data, the movement data, and the subjective data.

16. The method of claim 15, wherein the subjective data comprises a subjective sleep duration value, a reported number of awakenings, or a subjective sleep latency value.

17. The method of claim 11, wherein obtaining the respiratory data comprises estimating breathing rates and relative amplitudes for the periods of the measured data in which respiratory-related movement is predominant using a peak and trough identifying algorithm.

18. The method of claim 11 further comprising:
receiving, with the one or more processors, second measured data generated with a second non-contact sensor based on sounds associated with one or more coughs of the subject,
wherein the quality of life index is calculated based on the respiratory data, the movement data, and the second measured data.

19. The method of claim 18 further comprising:
generating, with the second non-contact sensor, the second measured data based on the sounds associated with the one or more coughs of the subject.

20. The method of claim 18, wherein the respiratory data includes respiratory effort data associated with the one or more coughs of the subject.

21. A system comprising:
a non-contact sensor configured to receive a signal reflected from a subject and obtain measured data from the reflected signal;
an input device configured to collect subjective data associated with the subject, wherein the subjective data comprises sleep quality data;
one or more processors; and
a non-transitory computer readable storage medium having instructions that, when executed by the one or more processors, cause the one or more processors to:
receive the measured data from the non-contact sensor;
receive the subjective data from the input device;
distinguish periods of the measured data in which respiratory-related movement is predominant from periods of the measured data in which bodily movement is predominant based on an amplitude value and a frequency value derived from the measured data;
obtain respiratory data from the periods of the measured data in which respiratory-related movement is predominant;
obtain movement data from the periods of the measured data in which bodily movement is predominant;
calculate a sleep quality of life (SQOL) index based on the subjective data, the respiratory data, and the movement data; and
generate feedback based on the calculated SQOL index.

22. The system of claim 21, wherein obtaining the respiratory data comprises estimating breathing rates and relative amplitudes for the periods of the measured data in which respiratory-related movement is predominant using a peak and trough identifying algorithm.

23. The system of claim 21, wherein the subjective data comprises a subjective rating indicating the subject's difficulty falling asleep, and wherein calculating the SQOL index comprises combining the subjective rating with a sleep efficiency value derived from the respiratory data and the movement data.

24. The system of claim 21, wherein the subjective data comprises a subjective sleep duration value, and wherein calculating the SQOL index comprises combining the subjective sleep duration value with an objective sleep duration value derived from the respiratory data and the movement data.

25. The system of claim 24, wherein a weighted sum is used to combine the subjective sleep duration value with the objective sleep duration value.

26. The system of claim 21, wherein the subjective data comprises a reported number of awakenings, and wherein calculating the SQOL index comprises combining the reported number of awakenings with an objective number of awakenings derived from the respiratory data and the movement data.

27. The system of claim 21, wherein the subjective data comprises a subjective sleep latency value, and wherein calculating the SQOL index comprises combining the subjective sleep latency value with an objective sleep latency value derived from the respiratory data and the movement data.

28. The system of claim 27, wherein a radical expression is used to combine the subjective sleep latency value with the objective sleep latency value.

29. The system of claim 21, wherein the feedback indicates whether a quantitative goal of a behavioral intervention program is achieved.

30. The system of claim 21, wherein the non-contact sensor is a biomotion sensor and the reflected signal is a radio-frequency signal.

31. The system of claim 21, wherein the non-contact sensor is an audio sensor and the reflected signal is a sound signal.

* * * * *